United States Patent [19]
Roundhill et al.

[11] Patent Number: 5,109,857
[45] Date of Patent: May 5, 1992

[54] ULTRASOUND TIME DOMAIN VELOCITY DETECTION METHOD AND APPARATUS

[75] Inventors: David N. Roundhill, Durham; Olaf T. von Ramm, Efland, both of N.C.

[73] Assignee: Duke University, Durham, N.C.

[21] Appl. No.: 664,021

[22] Filed: Mar. 4, 1991

[51] Int. Cl.$^5$ .............................................. A61B 8/02
[52] U.S. Cl. ........................... 128/661.08; 128/660.07; 73/861.25
[58] Field of Search ...................... 128/660.01, 660.02, 128/661.07, 661.08, 661.09, 661.10, 662.01; 73/861.25, 861.27

[56] References Cited

U.S. PATENT DOCUMENTS

| | | | |
|---|---|---|---|
| 4,693,319 | 9/1987 | Amemiya | 128/660.02 |
| 4,790,321 | 12/1988 | Miwa et al. | 128/660.07 |
| 4,840,180 | 6/1989 | Ito et al. | 128/661.08 |
| 4,853,904 | 8/1989 | Pesque | 128/661.08 |
| 4,866,613 | 9/1989 | Amemiya et al. | 128/661.08 |
| 4,993,417 | 2/1991 | Seo | 128/661.09 |

OTHER PUBLICATIONS

Angle Independent Ultrasonic Detection of Blood Flow, Trahey, Allison, von Ramm, IEEE Transactions on Biomedical Engineering, vol. BME-34, No. 12, Dec. 1987, pp. 965-967.
Ultrasonic Arteriography, Mozersky, Hokason, Baker, Sumner, Strandness, Jr. Arch Surg/vol. 103, Dec. 1971, pp. 663-667.
Color Digital Echo/Doppler Image Presentation, Eyer, Brandestini, Phillips, Baker, Ultrasound in Med. & Biol. vol. 7, pp. 21-31, 1981.
Multiple Cross-Beam Ultrasound Doppler Velocimetry, Fox, IEEE Transactions on Sonics and Ultrasonics, vol. SU-25, No. 5, Sep. 1978, pp. 281-286.
The Accurate Ultrasound Measurement of the Volume Flow of Blood By Time Domain Correlation, Embree and O'Brien, Jr., 1985 Ultrasonic Symposium, pp. 963-966.
Measurement of the Complete (3D) Velocity Vector of Blood Flows, Bonnefous, 1988 Ultrasonics Symposium, pp. 795-799.
Angle Independent Ultrasonic Blood Flow Detection by Frame-to-Frame Correlation of B-Mode Images, Trahey, Hubbard, von Ramm, Ultrasonics 1988, vol. 26, Sep. 1988, pp. 271-276.

*Primary Examiner*—Francis Jaworski
*Assistant Examiner*—George Manuel
*Attorney, Agent, or Firm*—Bell, Seltzer, Park & Gibson

[57] ABSTRACT

Disclosed is an ultrasonic method of measuring the movement of a particle in a test region. The method comprises processing a modulated signal returned from the test region to detect a first range of feature data and then processing a modulated signal returned from the test region to detect a second range of feature data. The second range of feature data is then compared to the first range of feature data to determine the positional displacement between at least one feature in the second range of feature data and the closest adjacent feature in the first range of feature data. The positional displacement indicates the movement of a particle in the test region. Also disclosed is an apparatus for carrying out the foregoing method.

30 Claims, 8 Drawing Sheets

ULTRASOUND TIME DOMAIN VELOCITY DETECTION METHOD AND APPARATUS

This invention was made with Government support under Grant No. CA 37586-10 awarded by the National Institutes of Health. The Government has certain rights to this Invention.

FIELD OF THE INVENTION

This invention relates to ultrasound in general, and particularly relates to a method and apparatus for measuring the movement of particles with ultrasound.

BACKGROUND OF THE INVENTION

From the earliest days of modern medicine the assessment of circulatory system viability has been of foremost concern to clinicians. If elements of the circulatory system become diseased the continued health of the tissues they supply is threatened. All manners of methods have been applied to the assessment of circulatory flow from non-invasive (requiring no physical insertion of instrument, a material or ionizing radiation) to highly invasive. Traditional non-invasive methods include plethysmography and ultrasound Doppler, see Mozersky et al, *Ultrasonic Arteriography*, Arch. Surg. Vol. 103, pp 663-667, Dec. 1971, while invasive methods range from thermodilution to the placement of electromagnetic flowmeters around individual blood vessels.

In recent years ultrasound has experienced considerable growth in clinical use. This growth is due in part to the development of color flow Doppler (see Eyer et al, *Color Digital Echo/Doppler Image Presentation*, Ultrasound in Med. & Biol., Vol. 7, pp 21-33 and Fox, *Multiple Crossed-Beam Ultrasound Doppler Velocimetry*, IEEE Transactions on Sonics and Ultrasonics, Vol. SU-25, pp 281-286), so called because the direction of flow in the body is displayed as a color superimposed on the tomographic display. In addition, ultrasound imaging has become widely accepted by the medical community because of its safety, ease of use and low cost. Color flow Doppler imaging provides a means of assessing blood flow in a two-dimensional tomograph, or slice through the body. This non-invasive, multi-dimensional, real-time measurement of blood velocity in the body provides a powerful clinical diagnostic tool. Despite the success of color flow Doppler processors, they suffer from certain major fundamental limitations. Color flow Doppler processors measure the axial component (along the beam) of the true velocity vector by detecting the frequency shift of the ultrasound transmit burst. Color flow Doppler processors do not measure the lateral or elevational vectors (across the beam). This approach to the analysis of flow fails to provide accurate perfusion rates because all three component vectors of the blood velocity must be known to calculate the flow from the velocity. Color flow Doppler processors frequently employ algorithms that impose a set of simplifying assumptions to estimate the actual flow present in the lumen, but they fall well-short of being able to provide accurate perfusion measurements in many common diagnostic situations.

In ultrasound velocity measurement, an ultrasound interrogation is performed by the transmission of an acoustic mechanical pulse into a test region or resolution volume A single interrogation consists of the transmission of a pulse of energy into the test region and the return of that energy from the test region. The electrical signal received from a pulse or series of pulses which interrogate a given area of the test region is called a line. Thus dividing the test region into one or more lines of interrogation. Interrogation is achieved in ultrasound by a transducer, excited by an electric pulse. The transducer converts the electrical energy into mechanical energy. The resolution volume is insonified, i.e. the mechanical energy is transmitted into the resolution volume. When the mechanical pulse impacts on an impedance boundary, some of the energy is reflected, some is transmitted and some is lost to absorption and scattering. Objects presenting an impedance boundary which scatters the incident wave are known as scatterers. The time between transmit and receive for a given target range is equal to C/2Z where C is the velocity of the sound in the body and Z is the target range. The factor of 2 results from the round-trip travel of the pulse to the target and back. When the reflected signal arrives back at the transducer the mechanical energy is converted back into electrical energy. The electrical signal may then be used for display purposes.

When a resolution volume containing a large number of scatterers is insonified, the resultant returned wave is a combination of constructive and destructive interference caused by the scatterers. This phenomenon was first described in the field of laser optics when it was observed that the light returning from an illuminated screen does not produce a uniform spot of reflected light. Instead a granular intensity variation, bearing no clear spatial relationship to the structure of the screen. As each scatterer reflects the incident waveform it modifies the amplitude and phase. The perceived signal is then the sum of all the individual reflected wavelets within a resolution volume. This summation process results in both constructive and destructive interference producing a random brightness pattern. Changes in this pattern result from changes in the distribution of scatterers in the illuminated field. If small changes in the distribution occur the pattern remains well correlated with the original pattern. The effect has been shown to occur in a similar fashion in ultrasound.

Considerable interest has been shown in tracking variations in amplitude of the resultant returned wave as it moves through the image with the motion of tissue and blood (see Embree et al, *The Accurate Measurement of the Volume Flow of Blood by Time Domain Correlation*, 1985 Ultrasonics Symposium, pp 963-966 and Bonnefous, Measurement of the Complete (3D) Velocity Vector of Blood Flows, 1988 Ultrasonics Symposium, pp 795-799). The primary attraction of this method of tracking is that it is inherently angle independent, in contrast to Doppler methods that require a component of the velocity to exist in the axial dimension. Work to date has focused on correlation processors in which a region of space is sampled in one acquisition and then tracked within the surrounding area by means of a correlation search process (see Trahey et al, *Angle Independent Ultrasonic Detection of Blood Flows*, IEEE Transactions on Biomedical Engineering, Vol. BME-34, pp 965-967 and Trahey et al, *Angle Independent Ultrasonic Blood Flow Detection Frame-to-Frame correlation of B-mode Images*, Ultrasonics 1988, Vol. 26, pp 271-276). The method has been proven in two dimensions using off-line simulations and has been implemented in a real time in one-dimensional processor (Philips Platinum CVI). Although correlation processors have been criticized because of the considerable computational complexity they have a more serious fundamental limitation. Correlation processors require kernel cells that must be tracked within the search region. In order for the correlation process to track successfully the form of the kernel must be unique among the closely surrounding regions. If the kernel is not unique the correlator will track to the wrong location. The need for a unique kernel dictates that the kernel must be at least two resolution cells long in any dimension tracking is to be performed. As the kernel cell size is increased, the imaging resolution decreases. Kernel cell size also presents particular problems at vessel walls where the kernel may include both stationary and moving amplitude variations. This problem is exacerbated by the need to use a kernel greater than the resolution cell size.

SUMMARY OF THE INVENTION

The present invention provides an ultrasonic method of measuring the movement of a particle in a test region. The method comprises processing a modulated signal returned from the test region to detect a first range of feature data and then processing a modulated signal returned from the test region to detect a second range of feature data. The second range of feature data is then compared to the first range of feature data to determine the positional displacement between at least one feature in the second range of feature data and the closest adjacent feature in the first range of feature data. The positional displacement indicates the movement of a particle in the test region.

In a more particular embodiment of the present invention, the method comprises processing a modulated signal returned from the test region to detect a first set of feature range data, the first set of data including the ranges of two adjacent features. The larger of the ranges is referred to as the distal range and the lesser of the ranges is referred to as the proximal range. Then, a modulated signal returned from the test region is processed to detect a second set of feature range data, the second set of data including a second range which is the range of a feature positioned between the proximal and distal ranges. The lesser displacement between the second range and the proximal and distal ranges is then determined, the lesser displacement indicating the direction and magnitude of movement of the particle in the test region.

The present invention also provides an apparatus for ultrasonically measuring the movement of a particle in a test region. The apparatus is adapted for use with a transducer which generates a signal in response to a modulated wave. The apparatus comprises a discriminating means adapted to be connected to the transducer for detecting a current feature in the signal generated by the transducer. Determining means are connected to the discriminating means for determining the range of the current feature. Storage means are connected to the determining means for storing the range. Comparing means are operatively associated with the storage means and the determining means for comparing the stored range to the range of a current feature to thereby determine the movement of the current feature.

In the same way that amplitude variations in the resultant returned wave was seen to be of value in correlation processors, the present invention provides a means by which variations may be tracked in a simpler way by the identification of waveform features and their subsequent tracking. For example, one such feature, waveform amplitude peaks, may be successfully identified and used as a flag that may be tracked from interrogation to interrogation. These and other aspects of the present invention are discussed in detail below.

DETAILED DESCRIPTION OF THE PREFERRED EMBODIMENTS

Figure 1:
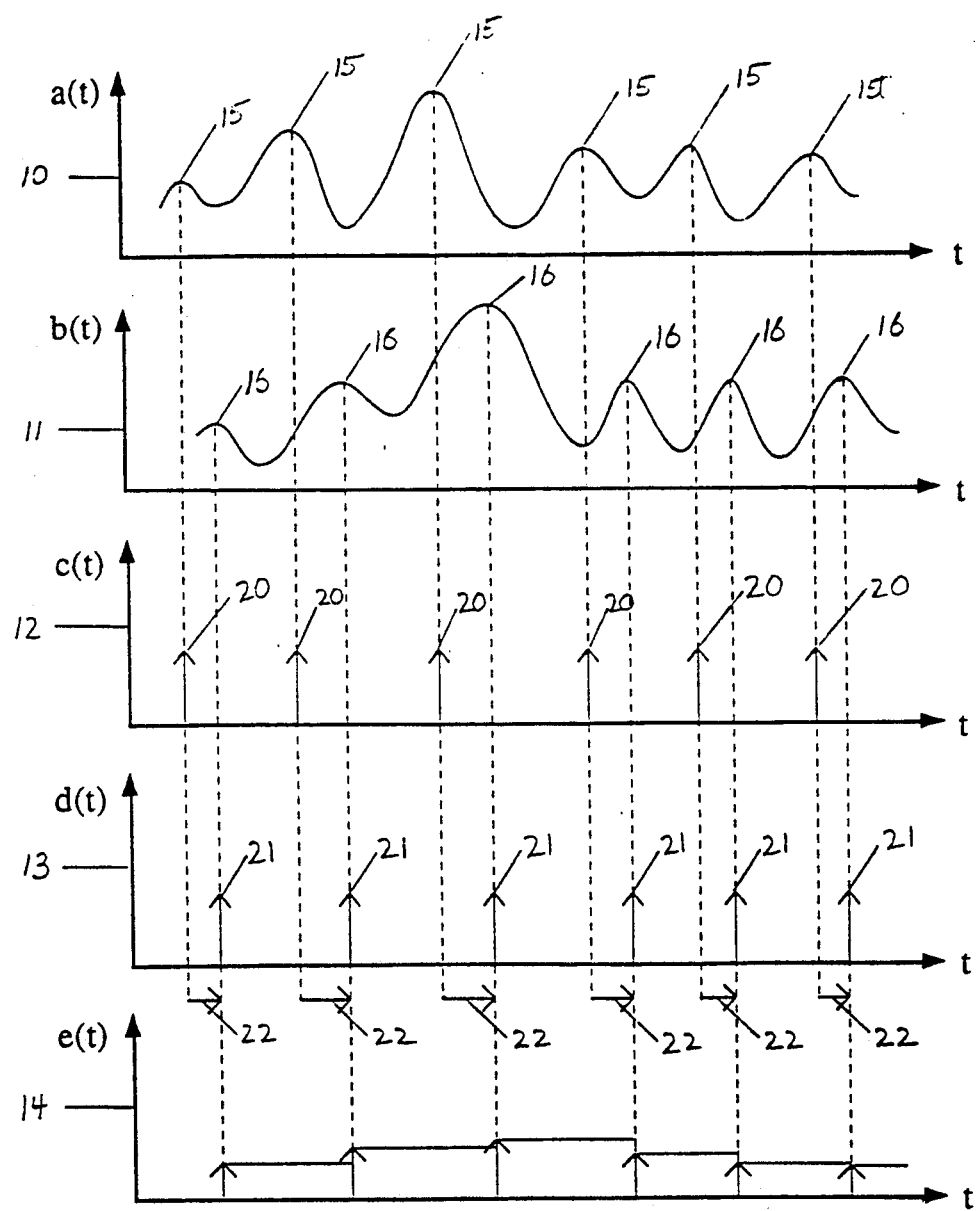
FIG. 1 is a graphical illustration of the feature tracking aspects of the present invention.

The term "test region" of the present invention is that area which is analyzed by the present invention to detect the movement or velocity of targets of interest. The test region interrogated by the present invention may include biological tissue such as animal tissue which may include blood and tumor tissue. The present invention is also useful in analyzing other biological tissues, including applications in renal, hepatic and cardiovascular analysis. The invention is also useful in obstetrics where the biological tissue may be a fetus and for the analyzing skulls in children and infants. The present invention is not limited to biological systems where movement is of interest, but may also be applied to other areas such as industrial applications, where flow measurements within a test region may consist of a pipe with fluid flowing within it.

Modulated signals which may be used in practicing the present invention may be generated in a number of ways, including exciting a transducer with a pulse or a frequency burst. When a frequency burst is employed, those frequencies used in medical diagnostic applications may be used (e.g., from about 1 MHz to about 25 MHz).

The term "feature", as used herein, means any distinguishable characteristic of the modulated signal that is spatially coherent, or spatially corresponds, with the waveform thereof. Examples of features which may be detected include amplitude peaks, amplitude troughs, amplitude peak/trough pairs or groups of amplitude peaks and troughs. Some methods for detecting such features include differentiation and convolution.

The time between the first and second processing steps may be predetermined. In general, when a source and a detector for the modulated signal are provided, the time between said processing steps should be not less than the time required for the modulated signal to travel from the source to the detector through the test region. With respect to a maximum time, the time between the processing steps should be less than the time required for the feature to move one half the distance to the closest adjacent feature. By "half the distance", we mean, for a given feature 20 as shown in FIG. 1, the displacement of the corresponding feature 21 is less than half the distance, as shown on the graph, to the next adjacent feature 20.

FIGS. 1 through 8 illustrate the operation of a specific apparatus of the present invention. The method employed for axial feature tracking in this apparatus uses, as the feature to be tracked, amplitude peaks in the resultant waveform produced by large numbers of scatterers within the resolution volume. A method of isolating a particular part of the resulting signal, referred to as feature discrimination is used. The axial range, measured in the time domain, of each detected feature is stored in memory as a digital number. When one line of feature range data has been stored in memory the same line is interrogated a second time. Thus the apparatus stores the first range of feature data between processing steps. The ranges of features occurring on the second interrogation are compared to those stored in memory by means of a range subtractor. The smallest distance between the present feature and those stored in memory is assumed to be the translation that the feature has undergone. Therefore, the relationship between time and position are known and the positional displacement indicates the velocity of a moving particle in the test region. The translation is then converted into an analog signal by means of a digital-to-analog converter. The direction of translation is determined at the same time.

FIG. 1 illustrates the use of feature detection to determine magnitude and direction of movement of a feature. Referring to FIG. 1, two sequentially occurring lines of detected r.f. are shown, lines a(t) 10 and b(t) 11. The lines of detected r.f 10 and 11 are then processed by the feature discriminator where, in the preferred embodiment, the peaks of the detected r.f. signals 15, 16 are detected. The output of the feature discriminator is shown for each as signals c(t) 12 and d(t) 13 which consist of a first series of pulses 20 representing the position of the peaks of the first line of detected r.f. 10 and a second series of pulses 21 representing the peaks of the second line of detected r.f. 11. The displacement 22 of each detected peak 15 is determined by subtracting the range of the detected peak 20 from the first line from the range of the detected peak 21 from the second line. The displacement of each peak 22 is represented by the amplitude of signal e(t) 14.

Figure 2:
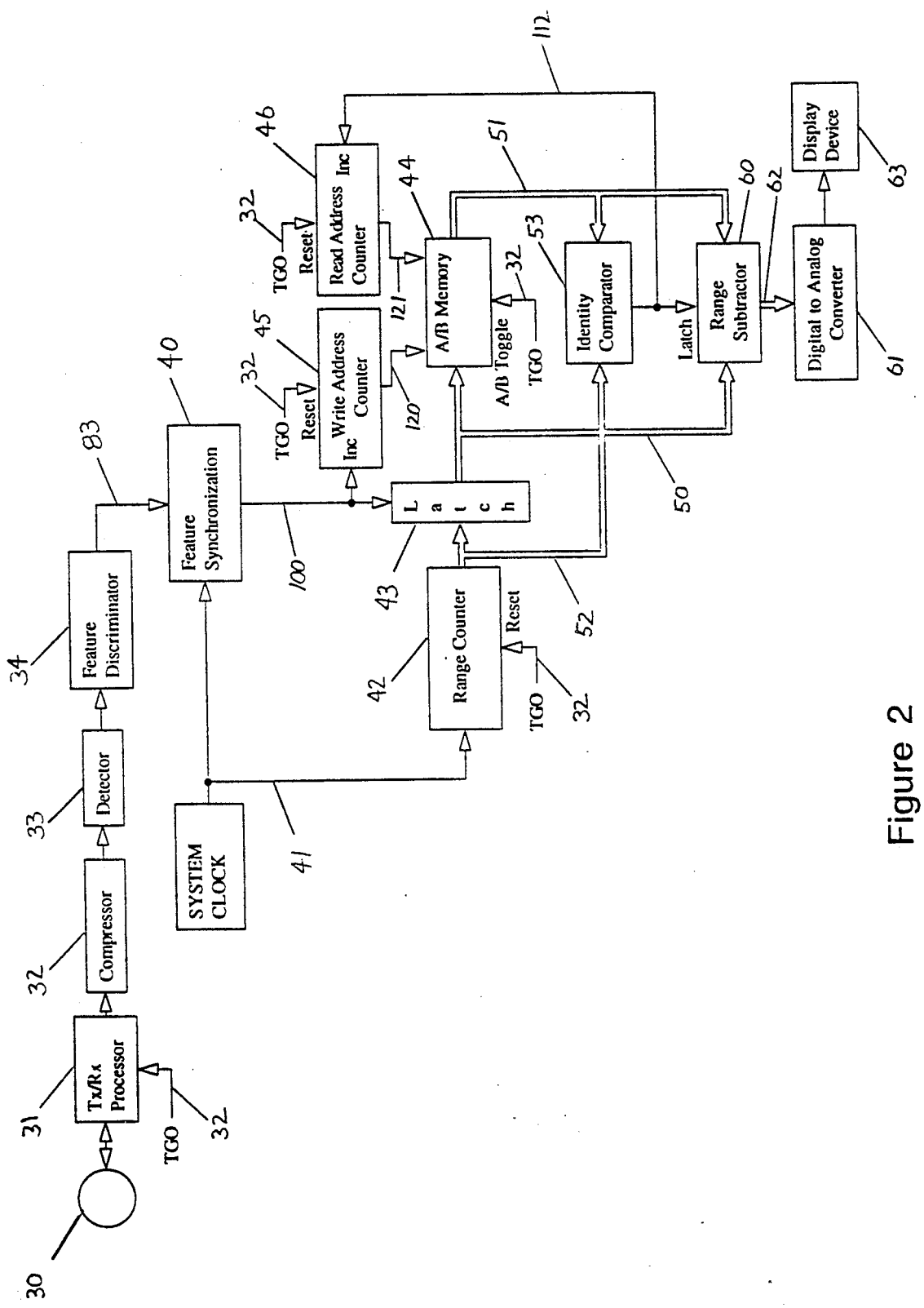
FIG. 2 is a block diagram of an apparatus of the present invention.

A block diagram of the preferred embodiment of the present invention is shown in FIG. 2. A focused piston piezoelectric transducer 30 manufactured by Aerotech is used to transmit an acoustic (mechanical) burst of energy into the test region. The same transducer is used to receive echoes from the test region and convert their energy back to an electrical signal.

A pulsed electrical transmitter contained within a transmit/receive processor 31 manufactured by Parametrics is employed to excite the transducer sufficiently to generate an acoustic transmit burst (typically the transmit voltage wave form applied is a short (typically about 50 ns) negative going pulse of between 50 and 150 volts). The transmit pulse is triggered by a TGO (Transmit GO) signal 32 that acts as a timing reference for most of the system. The same transducer 30 is used in transmit and receive therefore the transmit/receive processor 31 contains the necessary circuitry to amplify the low amplitude returning echoes. The received signal, commonly referred to as the received r.f. may, at this stage, be logarithmically compressed by the compressor or allowed to pass without compression. The signal is then input to the detector 33.

The purpose of the detector 33 is to remove the r.f. carrier frequency leaving the modulating signal intact. A full-wave rectifier is used to retain the energy from the negative going component of r.f. signal as well as the positive going r.f. signal.

The linear/compressed r.f. signal is band-pass filtered (pre-detection) and presented to the detector 33. A pre-detection filter is used to prevent the passage of very low frequencies, which would saturate the detection circuitry, and to filter out very high frequency noise. The r.f. signal is then full-wave rectified. After full-wave rectification the signal is low pass filtered to obtain the envelope function while rejecting the carrier frequency. The processed data is known as the detected r.f..

The purpose of the feature discriminator 34 is one of data compression The detected r.f. signal is received by the feature discriminator 34 from the detector 33, where it is processed to detect desired features of the detected r.f. signal. In the present embodiment the features detected are amplitude peaks of the detected r.f. signal which are detected through the use of a modified differentiator. The feature discriminator 34 then outputs a pulse for every feature detected. Data compression is achieved by assigning a single range to each feature, thereby reducing each feature of the wave-form to a single data point.

The feature synchronization 40 portion receives the output of the feature discriminator 34. The purpose of a feature synchronization scheme is to map the inherently unpredictable arrival of feature event timing into the digital domain. The digital system has a fundamental resolution limit defined by the frequency of the SYSTEM CLOCK 41. The incoming feature is mapped to the next occurring clock pulse, permitting a significant reduction in the complexity of digital design compared with a non-synchronous design approach, with no degradation of performance.

Each feature from the discriminator output is assigned a digital range that represents its position relative to the transmitted pulse. This is achieved by a range counter 42, which is reset at the beginning of each transmitted pulse and incremented at each rising edge of SYSTEM CLOCK until the next transmitted pulse. The count in the range counter 42 is transmitted across the range count data path 52 to latches 43 and stored when a feature is detected and synchronized. The latched count is subsequently written to the memory 44. The A/B memory 44 stores the range counts for further processing. An A/B memory configuration is used to permit simultaneous reading and writing. Data read from memory is that of ranges stored during the previous interrogation while the data written is that of the ranges of the current interrogation. Memory implementation is achieved with two identical banks of SRAM (static random access memory) configurations, memory A and memory B. The Write Address Counter 4S and the Read Address Counter 46 are reset with the transmission of each pulse by the TGO signal 32. The transmission of a pulse toggles the read/write modes of memory A and memory B. When memory A is write selected, memory B is read selected and visa versa. The transmission of a pulse also switches the read data path 51 to the memory bank which in read mode and the write data path So to the memory bank in write mode.

The range count in the latches 43 of each feature, or current feature range (CFR), is stored in memory 44. At the start of an interrogation line, i.e. when the TGO signal 32 initiated the transmission of a pulse, the range counter 42 is reset to zero and the Read Address Counter 46 is set to zero. The lowest value range from the previously interrogated line has been stored at memory address zero. The range value stored at the address selected by the read address counter 46 is presented through the read data path 51 as one input of an identity comparator The other input of the identity comparator 53 is the output of the range counter 42 which is received across the range count data path 52. The range counter 42 is incremented for each system clock 41 after the TGO signal 32. When the output of the range counter 42 is equal to the memory output the Read Address Counter 46 is incremented permitting the next stored range to be found. The stored range values, both before and after the Read Address Counter 46 is incremented, are latched into the Range Subtractor 60. In this manner the Range Subtractor 60 always has the closet range values greater than and less than the current feature range available for subtraction purposes.

The purpose of the range subtractor 60 is to identify and quantify the smallest translation that the feature may have undergone and to reject those values that are too large. The translation between the current feature and the closest feature in the previous lines represents the displacement of the feature. This translation data is sent to the Digital to Analog Converter 61 via the subtraction data path 62.

Figure 3:
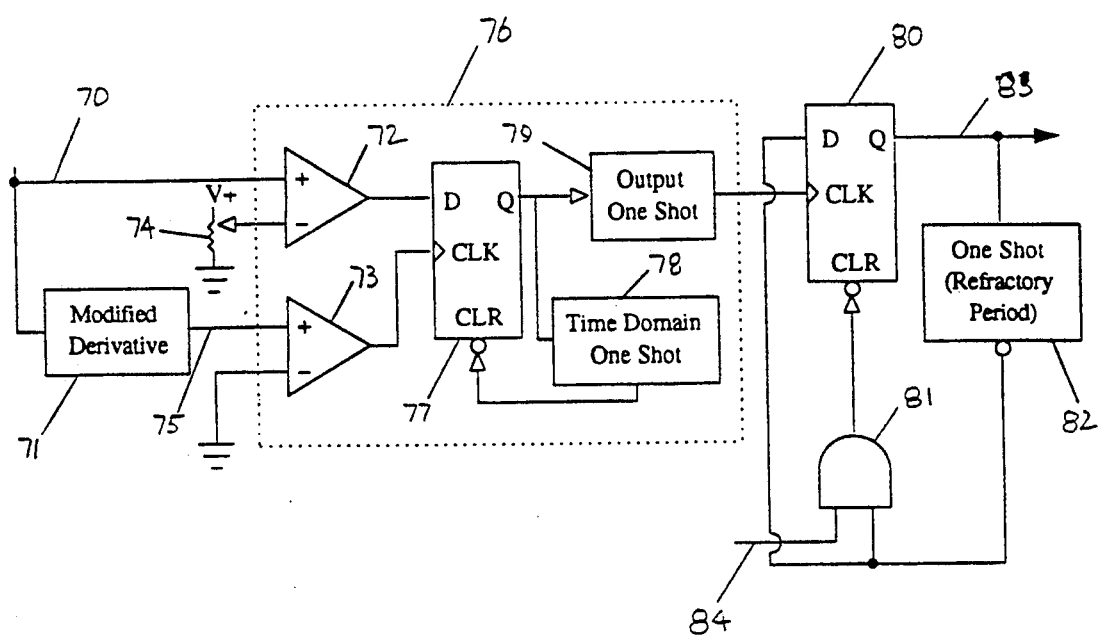
FIG. 3 is a schematic diagram of a specific implementation of the feature discriminator shown in FIG. 2.
Figure 8:
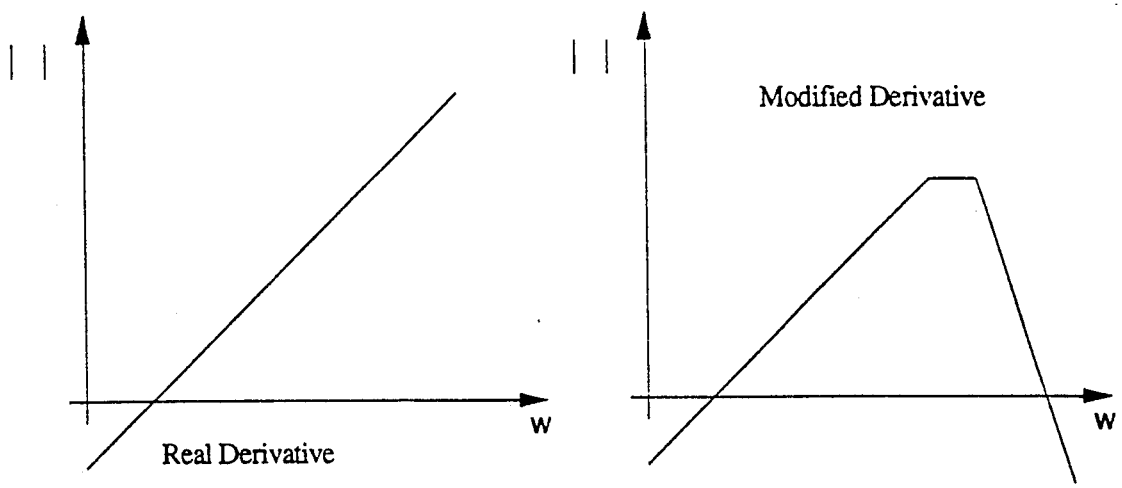
FIG. 8 is a graphical illustration of the transfer function in the frequency domain of the output of modified derivative element of FIG. 3.

The feature discriminator, shown schematically in FIG. 3, is an important stage in the tracking process. It is at this point where the detected r.f. data is reduced to a series of discrete events permitting substantial data reduction, but maintaining sufficient information to track motion of an insonified region. Feature discrimination is performed by a modified differential process that permits the extraction of peaks or troughs in the detected signal without the inherent susceptibility to high frequencies of a real differentiator. The modified derivative implemented by the differentiation circuit has an upper cut-off frequency to avoid amplification of frequencies above those of interest. The amplitude transfer function of this modified derivative is illustrated in FIG. 8. Any zero crossing of the differentiated signal causes the zero crossing comparator to fire. Only those zero crossings corresponding to a detected r.f. level exceeding a user adjusted reject level are allowed to pass on through the discriminator.

One specific implementation of the feature discriminator is shown in FIG. 3. The detected signal 70 is passed through a modified differential process whose transfer function is shown in FIG. 8 and both the undifferentiated 70 and differentiated 75 signals are applied to a signal processing device 76 to translate the amplitude peaks into a corresponding pulse. In the present embodiment, an Analog Devices AD 891 is used to process the differentiator output. Within the AD 891, one comparator 73 is used to detect the zero crossing points of the differentiator 71 while a second comparator 72 is used to check the level of the undifferentiated signal 70. In the event that a zero crossing occurs and the undifferentiated signal 70 exceeds a user set reject level, set by the resistance value 74, the AD 891 produces a pulse output.

Internally the AD 891 functions in the following way. When the amplitude of the undifferentiated signal 70 exceeds the reject level set by the resistance 74, the input to a D-type flip flop 77 is a logic 1. The zero crossing detector 73 produces a clock pulse every time the derivative signal 75 passes from a negative to a positive value (the modified derivative implementation is inverting to ensure polarity compatibility). The D input of the flip-flop 77 is connected to the output of the comparator 72 and is latched by the differentiated signal generated clock pulse. When the latched value is logic 1 and the Q output had been logic 0 the transition causes an output pulse to be produced by the output one shot 79. Any pulse occurring before the D-type flip flop 77 has been cleared will fail to cause an output trigger. The time after an output trigger during which another output trigger cannot occur may be thought of as a refractory period. Clearing of the D-type flip flop 77 is performed by the time domain one shot 78. When the reject level is not reached or exceeded by the undifferentiated signal 70 a logic zero is latched into the flip-flop 77. No output pulse occurs when the detected signal amplitude drops below the reject level.

An additional D-type flip flop 80 is used to extend the AD 891's relatively short maximum refractory period. During this time the feature discriminator is prevented from detecting additional features. This additional reject mechanism avoids excess noise signals, typically due to secondary triggering following a true amplitude peak, from appearing as recorded features. The length of the refractory period is user adjustable. Amplitude peak size is approximately equal to the resolution cell size and so amplitude peaks will typically be spaced approximately one pulse length of the point target response apart. The refractory period may be set to limit the occurrence of secondary triggering without rejecting excessive numbers of true amplitude peaks by setting the refractory period to be somewhat less than the pulse length. The refractory period is established by a one shot 82 which is triggered by the detection of a feature which is reflected as feature signal 83 which is the output of flip-flop 80. The output of flip-flop 80 is cleared between interrogation lines by the feature blanking signal 84 or during the interrogation line by the output of the one shot 82.

Figure 4:
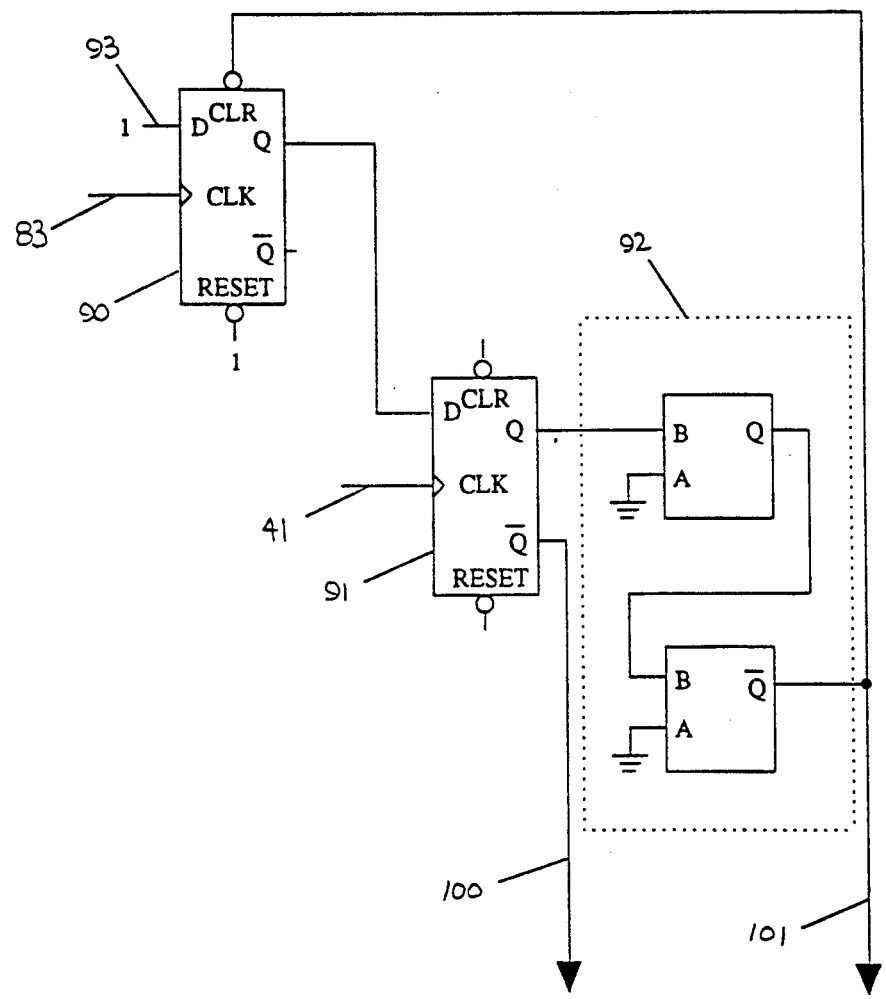
FIG. 4 is a schematic diagram of a specific embodiment of the feature synchronization element shown in FIG. 2.

Each feature detected by the feature discriminator is synchronized to the system clock 41. The specific implementation of the synchronization is shown in FIG. 4. Synchronization is achieved by two D-type flip flops. An incoming feature causes a transition on the feature signal 83 which causes the first flip flop 90 to latch a logic 1 that is hard wired at the input 93. When this latch has taken place the output of the first latch 90 is available for latching into the second flip flop 91. The rising edge of the system clock 41 (a 50 MHz free running ECL oscillator chosen for low noise) latches a logic 1 into the second flip flop and synchronization is achieved. The complementary output is used as the synchronous feature signal 100 (CF, for Current Feature). A monostable 92 is used as a timing device for the reset of the first flip flop 90 and the generation of a WRITE ENABLE 101 signal used to allow the range of the current feature (CF) to be stored in memory.

Figure 5:
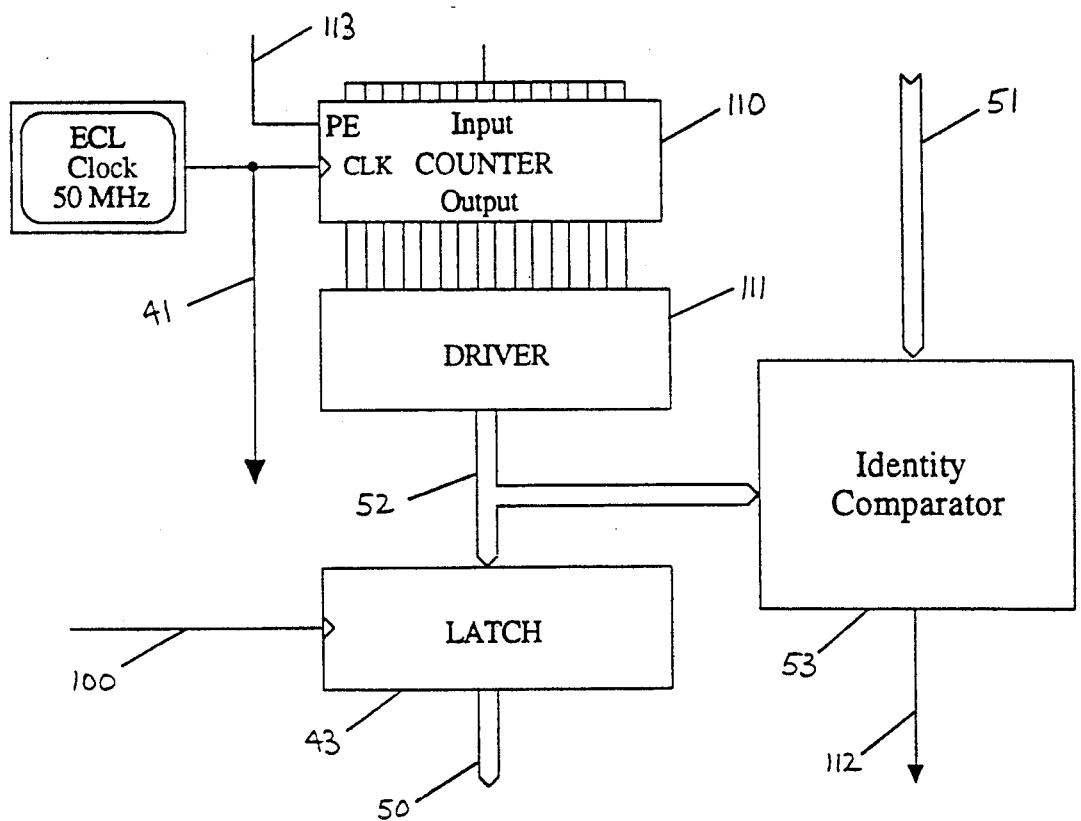
FIG. 5 is a schematic diagram of a specific embodiment of the range counter shown in FIG. 2.

A schematic diagram of the range counter 42 is shown in FIG. 5. A counter is reset at the beginning of each interrogation line by a line clear signal The counter is incremented with each occurrence of the system clock 41. The output of counter 110 is driven onto the range counter data path 52 by a set of drivers 113. The range counter data path connects drivers 111 to the latch 43 and the identity comparator 53. In this manner the current range value is available for comparison by the identity comparator 53 and to be latched as the range of a current feature when the synchronous feature signal 100 is activated. When the range count is equal to the range stored in the read memory at the address selected by the read address counter 46, the identity comparator 53 outputs an identity match signal 112.

Figure 6:
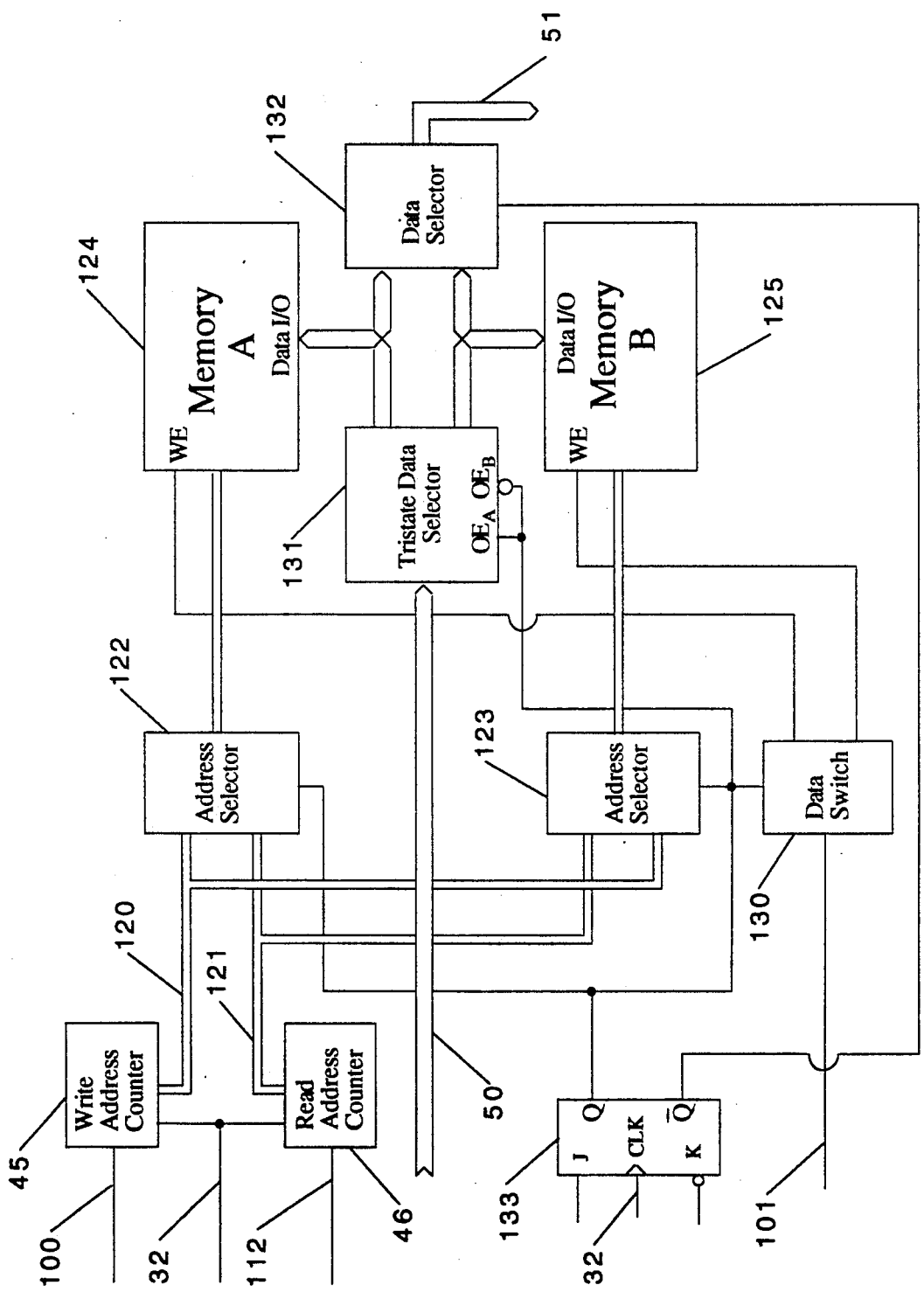
FIG. 6 is a schematic diagram of a specific embodiment of the A/B memory unit shown in FIG. 2.

The configuration of the A/B memory 44 is shown in FIG. 6. The write address counter 45 is incremented by the synchronous feature signal 100 and is reset by the TGO signal 32. The read address counter is incremented by the identity match signal 112 and is reset by the TGO signal 32. The read address and the write address are sent to an address selector 122 for the Memory A bank 124 and an address selector 123 for the Memory B bank 125. The write address is transmitted over a write address data path 120 and the read address over a read address data path 121 from the address counters to the address selectors. A J-K flip-flop is set to toggle its output with each TGO signal 32. The output of the J-K flip-flop 133 selects which bank of memory is read enabled or write enabled. Both the Q and Q not outputs of the J-K flip-flop 133 steer the direction of data and address to the memory banks for each interrogation line, switching one bank of memory from read to write and the other bank of memory from write to read. Flip-flop 133 controls data selector 131 for the range counter output 50 to direct the data to the bank of memory which is write selected. The complimented output of flip-flop 133 controls data selector 132 to direct the data from the memory bank which is read selected to the read data path 50. A data switch 130 directs the synchronous feature signal 101 to the write enable memory bank to store the feature range data presented on the range counter output data path 50 in the write enabled memory bank.

Figure 7:
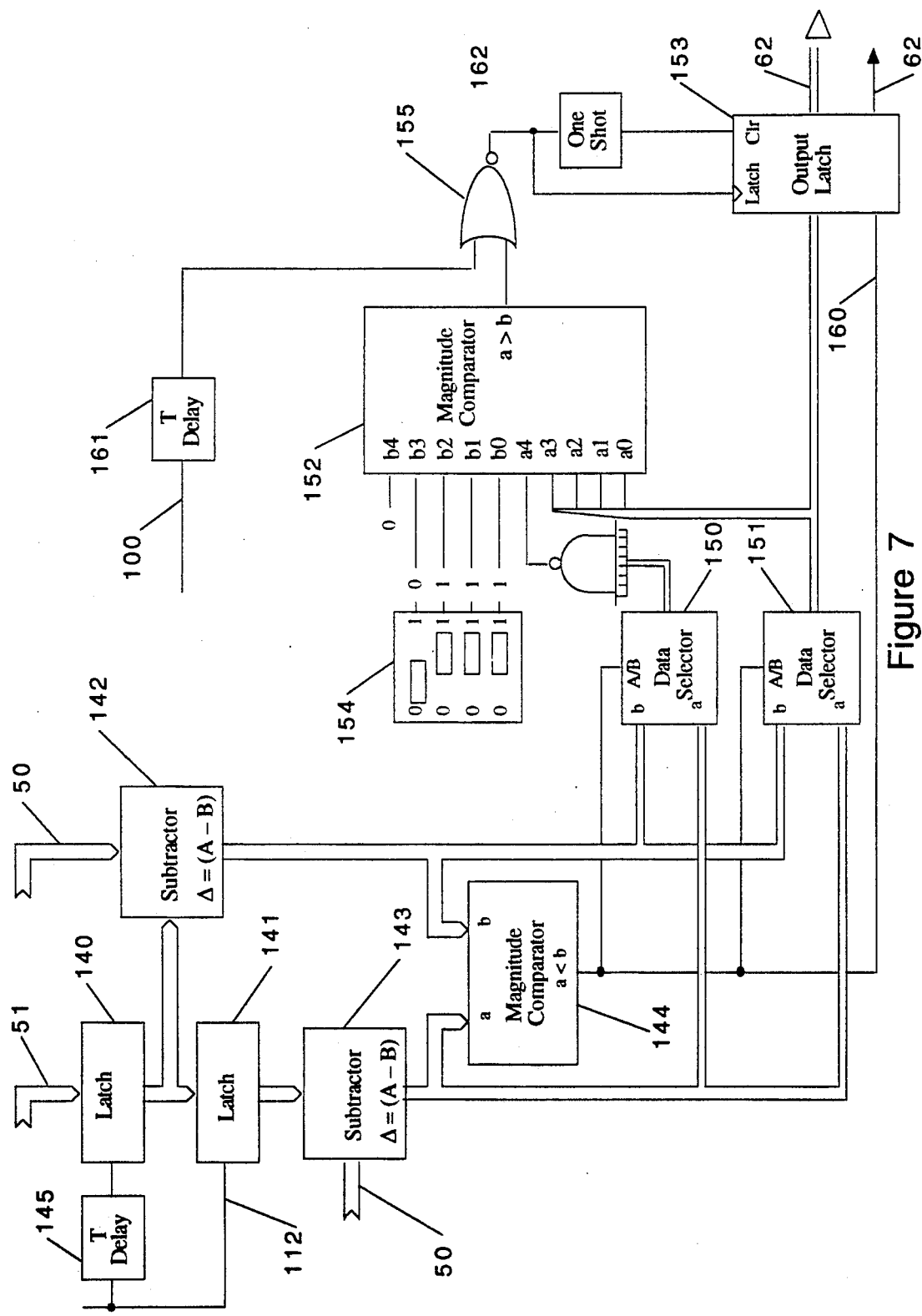
FIG. 7 is a schematic diagram of a specific embodiment of the range subtractor shown in FIG. 2.

Range Subtraction, is shown schematically in FIG. 7 and makes use of a 2-stage shift register to latch and store both the closest range less than the current range (proximal or PFR) and the closest range greater than the current range (distal or DFR) of the stored features being read from memory. Each time the range on the range counter output path 52 is equal to the range on the read data path 51, the identity comparator 53 outputs the identity match signal 112. The identity match signal 112 then clocks the existing distal range value stored in latch 140 into latch 141 which holds the proximate range value. The identity match signal is delayed by a delay element 145 and clocks the newly established distal range value into latch 140 from the read data path 51. At the same time that these ranges are brought into the Range Subtractor the range of features being detected along the current line (CFR) of interrogation are also presented to the subtractor from the write data path 50. The range subtractor subtracts the current range from the distal range to produce a first displacement, subtracts the proximal range from the current range to produce a second displacement and then compares the first and second displacements to find the lesser displacement. The Range Subtractor computes the value of (CFR-PFR) in subtractor 143 and (DFR-CFR) in subtractor 142. The outputs of the subtractors 142 and 143 are then compared in comparator 144 to determine which is smaller. The smaller result is then used as the translation value. The direction of flow is also determined by comparator 144 and reflected on the direction signal 160. The direction signal 160 controls data selectors 150 and 151 to select between the data from proximate subtractor 143 or distal subtractor 142. The output of data selector 150 is then used for magnitude comparison in the magnitude comparator 152. Differences exceeding the maximum, permissible value, which may be set using switches 154, are ignored while those within the limit are latched into the Range Subtractor output latch 153. If the magnitude is below the maximum permissible value then the comparator gates a delayed version of the synchronous feature signal 100 through a nor gate 155 and to the clock input of output latch 153. The synchronous feature signal 100 is delayed through delay element 161. The flow direction is determined by the sign (positive or negative) of the subtraction. The flow direction is used to direct the result of the subtraction to either the forward or reverse output channel. The output of data selector 151 is presented to the output latch 153 as the valid translation range. Both the direction and the translation are latched in the output latch 153. The clearing of the output latch 153 is accomplished by one shot 162.

Two digital to analog converters are used to convert the digital translation to analog values for display purposes. The use of two conversion channels permits the separation of forward flow and reverse flow. The direction signal from the Range Subtractor is used to direct the displacement to the appropriate output channel. The velocity data is displayed on separate channels of a Tektronix oscilloscope, triggered by the TGO signal 32, with the X axis as range and the Y axis as velocity. The choice of display device is not critical, and numerous other display means which provide useful clinical data are available. For example, velocity information could be coded in color and overlayed on a tomographic display.

The foregoing is illustrative of the present invention, and not to be construed as limiting thereof. For example, while an electrical apparatus has been described in detail above, it will be apparent that portions of this apparatus can also be implemented as optical systems. Those skilled in the art will also appreciate that this apparatus can be readily embodied on a single chip. The invention is accordingly defined by the following claims, with equivalents of the claims to be included therein.

That which is claimed is:

1. An ultrasonic method of measuring the movement of a particle in a test region comprised of biological tissue, the method comprising;
   processing a first occurrence of a modulated waveform signal returned from said test region and detecting a first range of feature data; and then
   processing a second occurrence of said modulated waveform signal returned from said test region and detecting a second range of feature data; then
   comparing said second range of feature data to said first range of feature data and determining the positional displacement between at least one feature in said second range of feature data and the closest adjacent feature in said first range of feature data;
   said positional displacement indicating the movement of a particle in the test region.

2. A method according to claim 1, further comprising the step of storing the first range of feature data between said processing steps.

3. A method according to claim 1, said positional displacement indicating the velocity of a moving particle in the test region.

4. A method according to claim 1 wherein said comparing step comprises the step of subtracting said first range of feature data from said second range of feature data.

5. A method according to claim 1 wherein said modulated signal comprises a pulse.

6. A method according to claim 1 wherein said feature comprises an amplitude peak.

7. An ultrasonic method of measuring the velocity of a moving particle in a test region comprising biological tissue, the method comprising:
processing a first occurrence of a modulated waveform signal returned from said test region and detecting a first set of feature range data, said first set of data including the ranges of two adjacent features, the larger of said ranges being a distal range and the lesser of said ranges being a proximal range; and then
processing a second occurrence of said modulated waveform signal returned from said test region and detecting a second set of feature range data, said second set of data including a second range which is the range of a feature positioned between said proximal and distal ranges; then
determining the lesser displacement between said second range and said proximal and distal ranges, the lesser displacement indicating the direction and magnitude of movement of the particle in the test region.

8. A method according to claim 7, wherein said determining step comprises the steps of:
subtracting said second range from said distal range to produce a first displacement; and
subtracting said proximal range from said second range to produce a second displacement; and then
comparing said first and second displacements to find the lesser displacement.

9. A method according to claim 7, further comprising the step of storing the first range of feature data between said processing steps.

10. A method according to claim 7 wherein said modulated signal comprises a pulse.

11. A method according to claim 7 wherein said feature comprises an amplitude peak.

12. An apparatus for ultrasonically measuring the movement of a particle in a test region, said apparatus adapted for use with a transducer, which transducer generates a signal in response to a modulated wave, the apparatus comprising:
discriminating means adapted to be connected to said transducer for detecting a feature in the signal generated by the transducer;
determining means connected to said discriminating means for determining the range of said feature;
storage means connected to said determining means for storing said range; and
comparing means operatively associated with said storage means and said determining means for comparing said stored range to the range of a second occurrence of said feature and for determining the movement of said feature.

13. An apparatus according to claim 12 wherein said discriminating means is a modified differentiator and wherein said feature is an amplitude peak in the signal generated by said transducer.

14. An apparatus according to claim 12 wherein said determining means is a range counter, said apparatus further comprising a system clock operatively associated with said range counter which increments said range counter.

15. An apparatus according to claim 12 wherein said comparing means comprises a subtractor for subtracting said range of said second occurrence of said feature from said stored range.

16. An ultrasonic method of measuring the movement of a particle in a test region comprised of biological tissue utilizing a source and detector for creating and detecting a modulated signal, the method comprising:
processing a first occurrence of said modulated signal returned from said test region to detect a first range of feature data; and then
processing a second occurrence of said modulated signal returned from said test region to detect a second range of feature data; wherein the time between said first occurrence and said second occurrence is less than the time required for a feature in said first range of feature data to move one half the distance to the closest adjacent feature in said first range of feature data and wherein the time between said first and second occurrences is not less than the time required for an occurrence of said modulated signal to travel from said source to said detector through said test region; then
comparing said second range of feature data to said first range of feature data to determine the positional displacement between at least one feature in said second range of feature data and the closest adjacent feature in said first range of feature data; said positional displacement indicating the movement of a particle in the test region.

17. A method according to claim 16, further comprising the step of storing the first range of feature data between said processing steps.

18. A method according to claim 16, said positional displacement indicating the velocity of a moving particle in the test region.

19. A method according to claim 16, wherein said comparing step comprises the step of subtracting said first range of feature data from said second range of feature data.

20. A method according to claim 16, wherein said modulated signal comprises a pulse.

21. A method according to claim 16, wherein said feature comprises an amplitude peak.

22. An ultrasonic method of measuring the velocity of a moving particle in a test region comprising biological tissue utilizing a source and detector for creating and detecting a modulated signal, the method comprising:
processing a first occurrence of a modulated waveform signal returned from said test region and detecting a first range of feature data, said first set of data including the ranges of two adjacent features, the larger of said ranges being a distal range and the lesser of said ranges being a proximal range; and then
processing a second occurrence of said modulated waveform signal returned from said test region and detecting a second range of feature range data, said second set of data including a second range which is the range of a feature positioned between said proximal and distal ranges; wherein the time between said first occurrence and said second occurrence is not less than the time required for said modulated signal to travel from said source to said detector through said test region, and wherein the time between said first occurrence and said second occurrence is less than the time required for said feature to move one half the distance to the closest adjacent feature in said first range of feature data; then determining the lesser displacement between said second range and said proximal and distal ranges, the lesser displacement indicating the direction and magnitude of movement of the particle in the test region.

23. A method according to claim 22, wherein aid determining step comprises the steps of:

subtracting said second range from said distal range to produce a first displacement; and subtracting said proximal range from said second range to produce a second displacement; and then comparing said first and second displacements to find the lesser displacement.

24. A method according to claim 22, further comprising the step of storing the first range of feature data between said processing steps.

25. A method according to claim 22, wherein said modulated signal comprises a pulse.

26. A method according to claim 22, wherein said feature comprises an amplitude peak.

27. An apparatus for ultrasonically measuring the movement of a particle in a test region, said apparatus adapted for use with a transducer, which transducer generates a signal in response to a modulated wave, the apparatus comprising:

discriminating means adapted to be connected to said transducer for detecting a feature in the signal generated by the transducer;

determining means connected to said discriminating means for determining the range of said feature;

storage means connected to said determining means for storing said range; wherein said storage means comprises two memory banks;

selecting mans for selecting one bank of memory as a read memory and one bank of memory as write memory; and comparing means operatively associated with said storage means and said determining means for comparing said stored range to the range of a second occurrence of said feature and for determining the movement of said feature.

28. An apparatus according to claim 27, wherein said discriminating means is a modified differentiator and wherein said feature is an amplitude peak in the signal generated by said transducer.

29. An apparatus according to claim 27, wherein said determining means is a range counter, said apparatus further comprising a system clock operatively associated with said range counter which increments said range counter.

30. An apparatus according to claim 27, wherein said comparing means comprises a subtractor for subtracting said range of said second occurrence of said feature from said stored range.

* * * * *